(12) United States Patent  (10) Patent No.: US 7,522,834 B2
Heaven et al.  (45) Date of Patent: Apr. 21, 2009

(54) CAMERA HOUSING WITH SELF-CLEANING VIEW PORT

(75) Inventors: Edwin Michael Gyde Heaven, North Vancouver (CA); Patrick Koropatnick, West Vancouver (CA); Kari Kristen Hilden, West Vancouver (CA)

(73) Assignee: Papertech Inc., North Cancouver, British Columbia (CA)

( * ) Notice: Subject to any disclaimer, the term of this patent is extended or adjusted under 35 U.S.C. 154(b) by 380 days.

(21) Appl. No.: 11/367,159

(22) Filed: Mar. 3, 2006

(65) Prior Publication Data

US 2007/0206942 A1 Sep. 6, 2007

(51) Int. Cl.
G03B 17/02 (2006.01)
H04N 5/225 (2006.01)
(52) U.S. Cl. .................................. 396/535; 348/373
(58) Field of Classification Search ................. 396/287, 396/535, 537; 348/373, 374
See application file for complete search history.

(56) References Cited

U.S. PATENT DOCUMENTS

| | | | |
|---|---|---|---|
| 4,521,089 A * | 6/1985 | Bohl et al. | 359/507 |
| 4,969,035 A | 11/1990 | Dawson | |
| 5,394,208 A | 2/1995 | Campbell | |
| 5,831,668 A | 11/1998 | Hirvonen et al. | |
| 6,091,444 A | 7/2000 | McCarville et al. | |
| 6,362,889 B1 | 3/2002 | Mustonen | |
| 6,778,209 B1 * | 8/2004 | Eversole et al. | 348/83 |
| 2001/0013892 A1 | 8/2001 | Eversole et al. | |
| 2003/0210906 A1 | 11/2003 | Peterson et al. | |
| 2005/0276599 A1 | 12/2005 | Kajino et al. | |

FOREIGN PATENT DOCUMENTS

JP 2004-109828 4/2004

OTHER PUBLICATIONS

Papertech Webvision Plus Product Release entitled "Next Generation WebView™ Camera Housing" dated Jul. 22, 2004.
Transmittal and International Search Report and Written Opinion issued Jun. 12, 2007 in connection with PCT Patent Application No. PCT/CA2007/000349.

* cited by examiner

Primary Examiner—Rodney E Fuller
(74) Attorney, Agent, or Firm—Kolisch Hartwell, P.C.

(57) ABSTRACT

Apparatus for maintaining an unobstructed view for visual monitoring equipment comprises a housing to isolate the visual monitoring equipment from an external environment. An inlet to the housing is connectable to a source of gas under pressure for cooling and cleaning purposes. At least one outlet to the housing defines a view port to allow the visual monitoring equipment to acquire images external to the housing and to allow gas to exit the housing. The outlet constricts the flow of gas leaving the housing resulting in acceleration of the gas through the outlet to form an exit jet that maintains the outlet unobstructed by debris. The housing is simple in construction with few moving parts resulting in reliable and efficient operation.

15 Claims, 4 Drawing Sheets

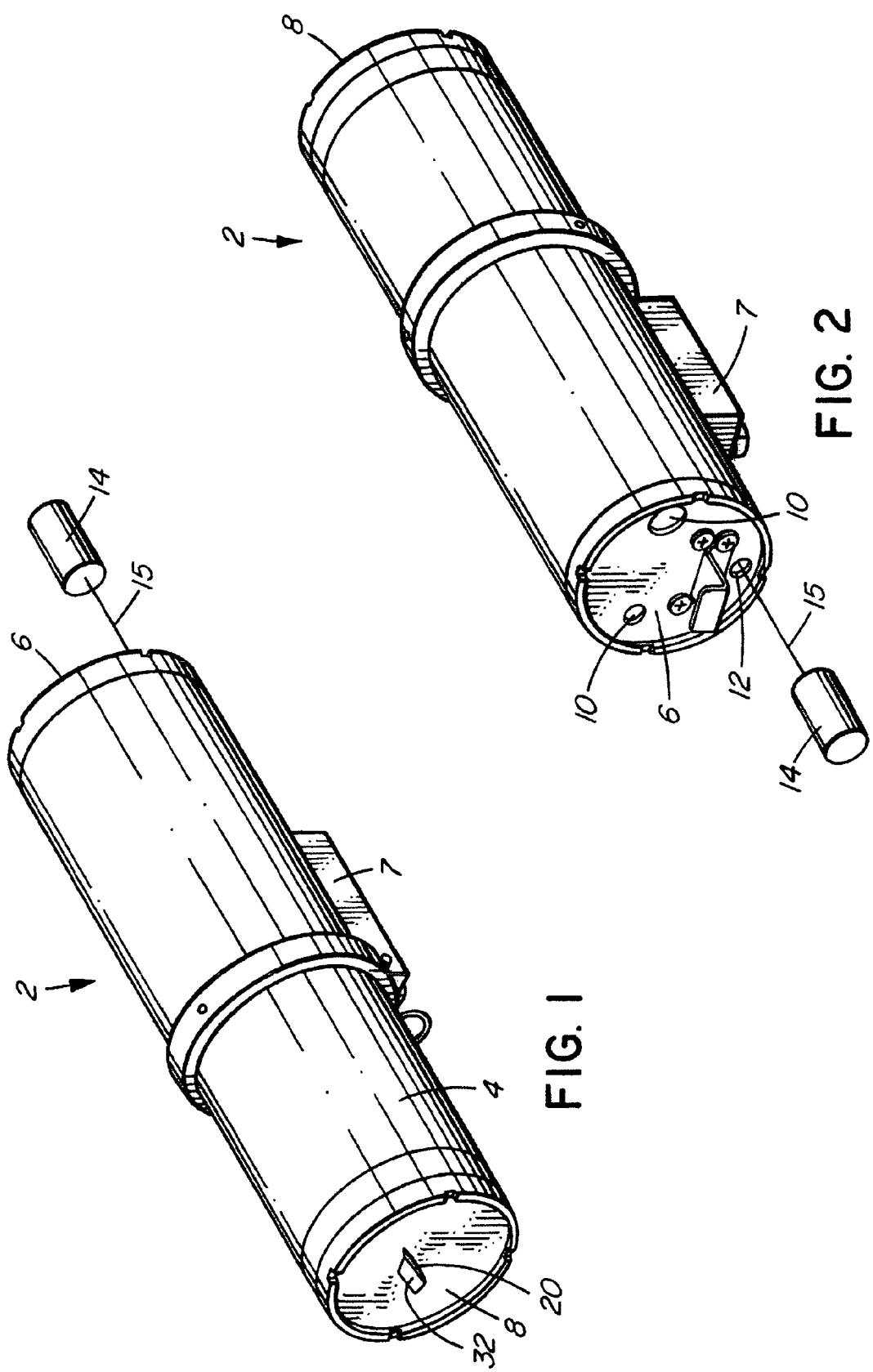

CAMERA HOUSING WITH SELF-CLEANING VIEW PORT

FIELD OF THE INVENTION

This invention relates generally to visual monitoring systems used to observe a site of interest, particularly in industrial processes, and, more particularly to a housing for an image capturing camera that protects the camera from the environment external to the housing and maintains an unobstructed view port for the camera.

BACKGROUND OF THE INVENTION

Visual monitoring systems, particularly those developed for use in industrial environments where conditions for observation of objects of interest are often detrimental to reliable viewing, generally require means to maintain a clear view of the objects of interest. These environments commonly have ambient conditions that result in the monitoring equipment being coated in short order in layers of opaque material that are by-products of the industrial process under observation. For example, in the paper making industry, stray paper fibres that are an inevitable part of the manufacturing process tend to be deposited on, and build up to cover all stationary equipment adjacent to the processing line. The ambient conditions are also inappropriate for reliable operation of electronic monitoring equipment such as video or still cameras. The environments can include high temperatures, caustic or corrosive atmospheres, condensing liquid and directed sprays, and mechanical contaminants and debris that will individually or in combination cause the camera equipment to malfunction or to fail to provide the required view.

Visual monitoring systems will typically protect the image acquisition equipment or camera in an enclosure to provide means to control the environment in which the camera operates. This enclosure is substantially sealed from the external environment and is equipped with a covered view port through which the camera can capture images of the external environment. Generally, the enclosure will have a manual or automatic system to maintain a clear view port for the camera. Many such systems rely on recessed view ports and/or a sheet of air that is operated intermittently or continuously to prevent debris or other contaminants from blocking the view port. For example, U.S. Pat. No. 4,969,035 to Dawson discloses the use of a gas jet to prevent blocking of a pin hole aperture adjacent a camera window with debris to permit viewing of the interior of a furnace or similar high temperature environment. Published US Patent Application No. 20030210906 to Peterson et. al. teaches the use of intermittent bursts of air to clean a cover positioned adjacent a camera protected with an enclosure. Published US Patent Application No. 20050276599 to Kajino et al. discloses the use of air streams directed past the lens of a camera sealed in a housing to prevent condensation built up from blocking the view of the camera.

In another approach, U.S. Pat. No. 5,394,208 to Campbell discloses an enclosure for a camera that relies on creation of a pressurized enclosure interior and formation of a vortex flow through a camera view port in the enclosure to prevent blocking of the view port.

U.S. Pat. No. 6,362,889 to Mustonen shows the use of a continuous air stream that flows through a camera housing and across the camera lens to prevent accumulation of blocking debris.

SUMMARY OF THE INVENTION

The present invention employs a new approach that relies on a high velocity jet of air exiting from a pressurized housing to maintain a clear and unobstructed view port for visual monitoring equipment mounted inside the housing.

Accordingly, the present invention provides apparatus for maintaining an unobstructed view for visual monitoring equipment comprising:

a housing to isolate the visual monitoring equipment from an external environment;

an inlet to the housing connectable to a source of gas under pressure;

at least one outlet to the housing defining a view port to allow the visual monitoring equipment to acquire images external to the housing and to allow gas to exit the housing, the at least one outlet constricting the flow of gas resulting in acceleration of the gas through the outlet to form an exit jet that maintains the outlet unobstructed.

The pressurized gas serves the dual function of cooling the visual monitoring equipment and creating a cleaning jet that keeps the viewing aperture unobstructed by debris and prevents contamination of the interior of the housing.

BRIEF DESCRIPTION OF THE DRAWINGS

Aspects of the present invention are illustrated, merely by way of example, in the accompanying drawings in which:

FIG. 1 is a perspective view of a camera housing according to a preferred embodiment of the present invention from a first end showing the camera view port;

FIG. 2 is a perspective view of the camera housing of FIG. 1 from an opposite second end showing access ports to the interior of the housing;

DESCRIPTION OF THE PREFERRED EMBODIMENTS

Figure 3:
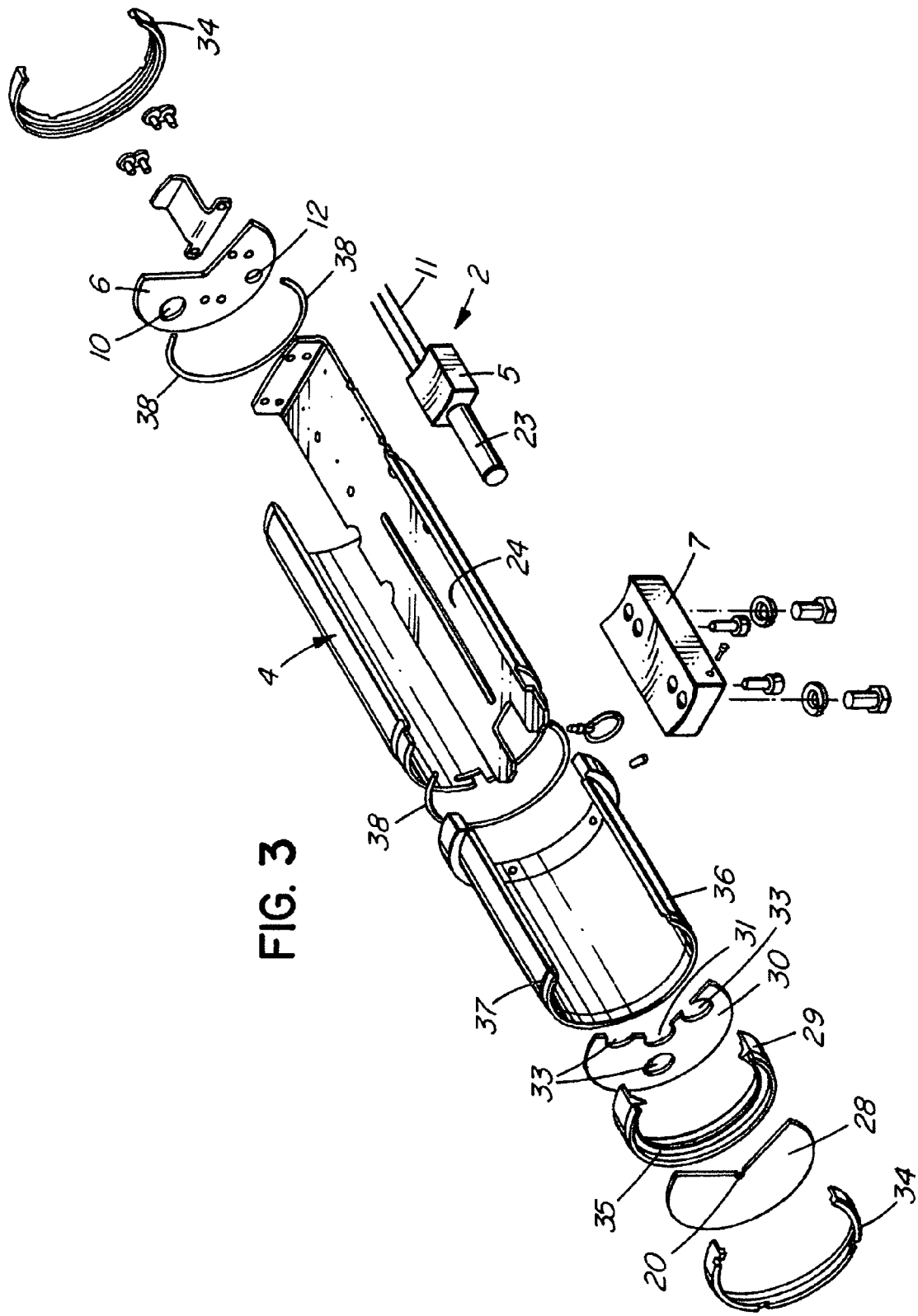
FIG. 3 is an exploded view of the camera housing according to a first embodiment.

Referring to FIGS. 1 and 2, there is shown a first embodiment of the apparatus 2 of the present invention for maintaining an unobstructed view for visual monitoring equipment. The apparatus is intended for use particularly in industrial processes for monitoring various manufacturing processes and equipment in environments which may include high temperatures, caustic or corrosive atmospheres, condensing liquid and directed sprays, and mechanical contaminants and debris that will individually or in combination cause unprotected monitoring equipment to malfunction or to fail to provide the required view. It will be understood that the apparatus of the present invention finds application in any environment where reliable monitoring of a process is required.

The apparatus 2 generally comprises a housing 4 to isolate the visual monitoring equipment from an external environment. The visual monitoring equipment 5 (FIG. 3) may include a video or still photography camera such as a CCD array analog or digital camera or any other equipment capable of providing image data. In the illustrated embodiment, the housing comprises a generally cylindrical enclosure having a first end 6 and second end 8. First end 6 is formed with a plurality of access ports 10 to allow access to the interior of the housing for lines 11 providing power and control signals to the visual monitoring equipment 5 mounted within the interior of the housing. Access ports 10 also accommodate video signal lines that transmit image data collected by the monitoring equipment 5. Lines 11 are sealed at their point of entry into first end 6 using standard sealing techniques. The exterior of housing 4 includes a mounting bracket 7 to allow the housing and camera to be conveniently mounted at the desired angle to a location on the equipment being monitored. It will be understood that alternative mounting brackets or arrangements are possible.

First end 6 also includes a housing inlet 12 connectable to a source of gas under pressure 14 via line 15. The pressurized gas introduced into the interior of the casing via inlet 12 serves to maintain the temperature of the interior within an acceptable temperature range for reliable operation of the visual monitoring equipment 5. In many cases, this will involve the pressurized gas cooling the camera equipment, but it is also possible in very cold environments that the pressurized gas will perform a warming function. In many applications, the source of gas under pressure 14 will comprise a source of filtered air, however, it will be readily apparent to a person skilled in the art that other gases can be used.

The second end 8 of housing 4 is formed with at least one outlet 20 which defines a view port to allow the visual monitoring equipment 5 to acquire images of a site of interest external to the housing. Outlet 20 also allows the pressurized gas entering the housing via inlet 12 to exit the housing. Outlet 20 is dimensioned to constrict the flow of gas exiting the housing with the result that the gas is accelerated through outlet 20 to form an exit jet that maintains the outlet clear and unobstructed by debris or other contaminants.

In a preferred arrangement, outlet 20 comprises a pinhole aperture having a diameter in the range of about 1 to 10 mm. Such an arrangement uses visual monitoring equipment in the form of a camera 5 equipped with a pinhole lens 23 selected to match the dimensions of the pinhole aperture. Pinhole lens 23 can be a fixed, varifocal, or zoom lens.

In an alternative embodiment, outlet 20 comprises a larger opening having a diameter in the range of about 11-50 mm. In this arrangement, the visual monitoring equipment can be a camera that uses a larger lens such as an 8-48 mm zoom lens selected to match the dimensions of the opening.

In all cases, the lens of the camera is positioned adjacent the outlet 20 to achieve a clear, preferably wide angle, view through the outlet. To facilitate proper positioning of the camera within the housing, an elongate mounting plate 24 is optionally provided to permit slidable movement of the camera along the longitudinal axis of the housing such that the lens is properly positioned directly behind outlet 20.

In the first embodiment of FIG. 3, the second end 8 of housing 4 is formed from a generally circular end plate 28 formed with a central outlet 20. Plate 28 is retained against retaining ring 29 by an outer locking ring 34. Internal to plate 28, an inner circular plate 30 is provided having a plurality of holes therethrough. Central hole 31 provides an opening through which pinhole camera lens 23 protrudes to allow the plate to stabilize and support the lens. The other holes 33 provide passages through plate 30 for flow of pressurized gas to the second end 8 of the housing. Retaining ring 29 is formed with an inwardly extending shoulder 35 against which inner plate 30 abuts when retaining ring 29 is fitted over an edge 37 of the housing.

To ensure reliable operation, the housing of the present invention requires must be sealed and pressurized during normal operation to ensure that contaminants do not enter the interior of the housing. In this respect, O-ring seals are preferably used between sections of the housing to ensure an adequate seal. In addition, outlet 20 preferably includes a mechanism to ensure that contaminant ingress is prevented in the event that the supply of pressurized gas is lost. This may take many forms depending on the internal configuration of the apparatus. For example, a one way valve 32 or pressurized release plug may be used. Where the internal components are not affected by the external contaminants, the return of air pressure will self-clear the opening. If the internal components are affected by contaminants, then they need to be protected from the ingress of contaminants by a physical barrier such as internal component housings, internal component enclosures, internal component protective covers, or barriers at the outlet which will interpose themselves when pressure is lost but not obstruct the view through the opening. By way of example, the visual monitoring equipment 5 and the attached lens 23 may be independently sealed using a waterproof material against any potential contaminant ingress into the housing from the external environment.

Figure 4:
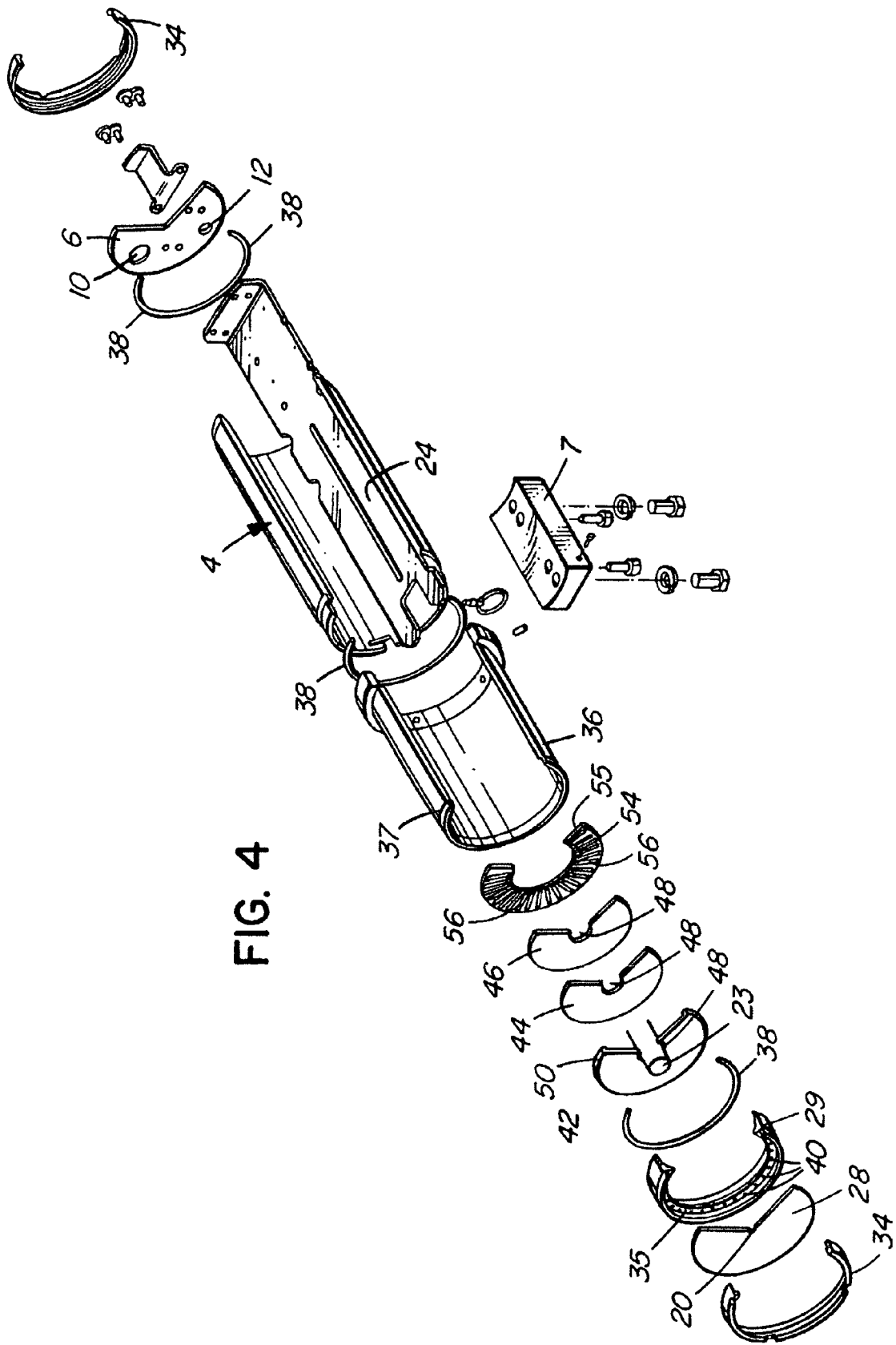
FIG. 4 is an exploded view of the camera housing according to a second embodiment including a sealing system to prevent contamination of the interior of the housing.
Figure 5:
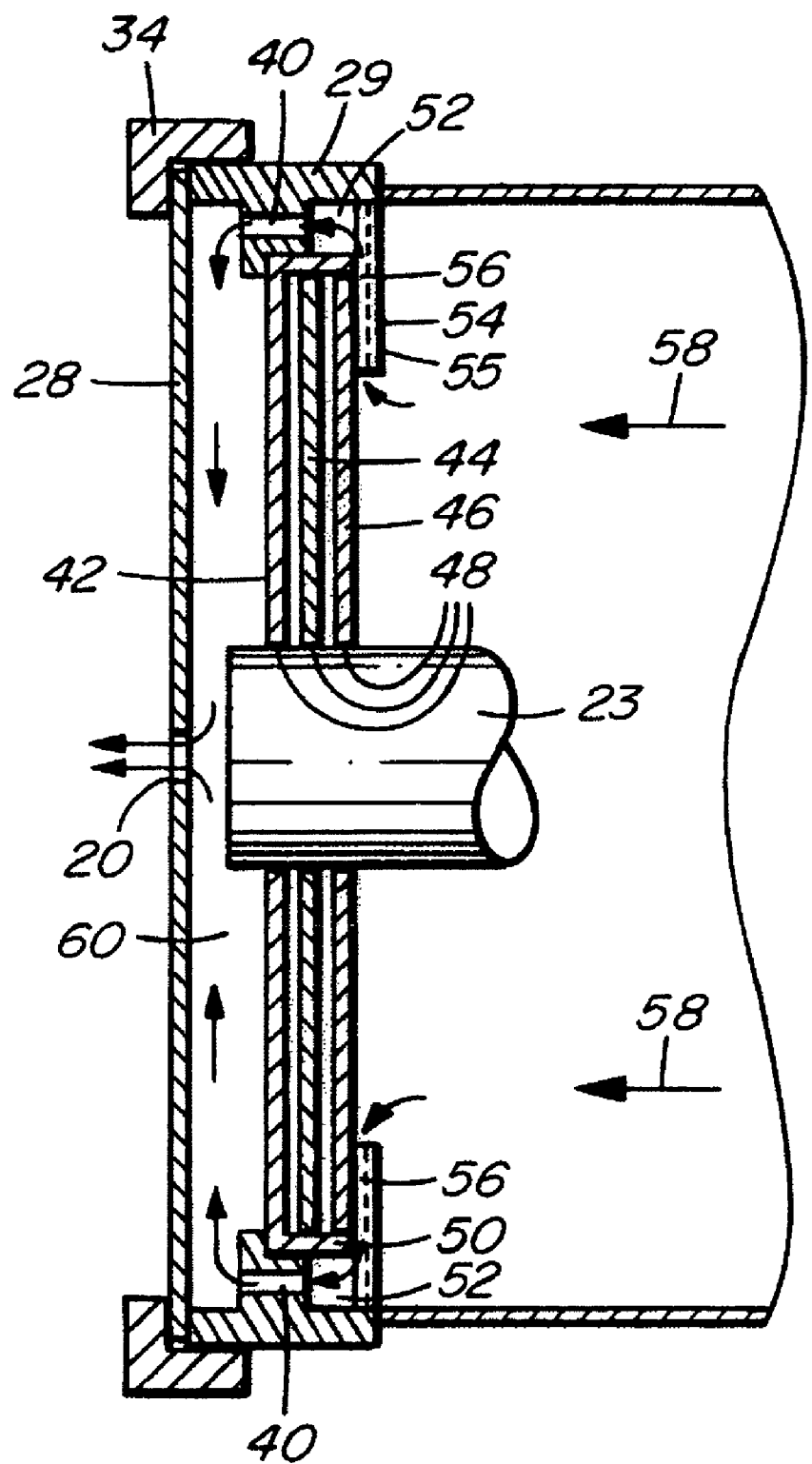
FIG. 5 is a detail sectioned view through the sealing system.

FIGS. 4 and 5 show a second embodiment of the apparatus of the present invention which includes an exemplary sealing system for preventing contaminants from entering the housing in the event that the supply of pressurized gas is lost. Parts of the apparatus that are identical to the parts of the first embodiment are identified by the same reference number. In the second embodiment, the second end 8 of the housing 4 includes a plate 28 with outlet 20 which is retained against an edge of retaining ring 29 by locking ring 34. In this case, the inwardly extending shoulder 35 of retaining ring 29 is formed with a plurality of passages 40 to allow pressurized air to flow through the shoulder. In this embodiment, the open centre of retaining ring 29 is blocked by a series of plates and gaskets that fit about the camera lens 23 to prevent contaminants from entering the housing. In particular, the open centre of retaining ring 29 is blocked by a front gasket holder 42, a flexible gasket 44, and a gasket spacer ring 46 which are all formed with aligned central openings 48 to accommodate lens 23 of the camera. The front gasket holder 42, flexible gasket 44 and gasket spacer ring 46 co-operate to define a sealing element within the housing through which the lens 23 of the camera protrudes. The sealing element acts to separate the interior of the housing into a first region adjacent the outlet into which contaminants can infiltrate in the event of a loss of gas pressure and a second, sealed region which is always free of contaminants.

Optionally, front gasket holder 42 is formed with a rearwardly extending edge 50 into which gasket 44 and gasket spacer ring 46 fit to form a combined sealing unit. This sealing unit fits over camera lens 23 which protrudes through the aligned central openings 48 of the individual elements. Flexible gasket 44 performs the sealing function while rigid front gasket holder 42 and rigid gasket spacer ring 46 support the gasket therebetween. The front gasket holder and gasket space ring also act to support the camera lens extending therethrough.

A labyrinth gas flow diversion passage is created about the outer perimeter of the sealing element to permit flow of gas under pressure out of the housing while preventing contaminants from entering the second, sealed region of the housing in the event that gas pressure is lost. Front gasket holder 42 is shaped and dimensioned to fit against an inner side of shoulder 35 of retaining ring 29 to define an outer annular region 52 between gasket holder edge 50 and retaining ring 29. Annular region 52 is best shown in FIG. 5 which is a cross-sectional view of the assembled sealing system. To divert pressurized gas into annular region 52, a flow diversion ring 54 is mounted in front of gasket spacer ring 46. Flow diversion ring 54 comprises a flat, annular body 55 with a central opening for the passage of pressurized gas. The face of annular body 55 immediately adjacent gasket spacer ring 46 is formed with a series of radial channels 56 that extend from the inner edge of the opening of the body to the outer edge. As shown by arrows 58 in FIG. 5, pressurized gas flowing parallel to the longitudinal axis of the housing is diverted to flow radially outwardly when the flow reaches gasket spacer ring 46. The diverted gas flow is directed by radial channels 56 into annular region 52. Passages 40 through shoulder 35 allow the diverted flow to exit annular region 52 into the region 60 behind end plate 28. The pressurized gas then flows through outlet 20 as a jet which maintain the outlet clear of debris.

In the event that gas pressure is lost, any contaminants that enter outlet 20 will tend to be confined in region 60 between end plate 28 and front gasket holder 42. Passages 40 are dimensioned to permit free flow of gas under pressure, however, any contaminants such as liquids or particles will tend not move through the passages toward the sealed interior of the housing. When gas pressure is restored, the gas flow will tend to eject any contaminants back out outlet 20 in a self-cleaning operation.

As shown in FIG. 3 or 4, the apparatus of the present invention, particularly housing 4, is optionally of a modular construction to allow interchanging of different parts. For example, ends 6 and 8 of the housing are preferably circular plates that are sealably fastened into place using O ring seals 38 in combination with threaded or snap on retaining rings 34. This allows for different end plates formed with differently dimensioned outlets 20 or access ports 10 to be used in the event that the camera 5 within the housing is changed. Section 36 of housing 4 can also be formed into different lengths or multiple sections can be stacked together to vary the overall length of the housing to accommodate camera and lens units of different longitudinal dimensions. This provides further flexibility in ensuring that the camera lens 23 is always positioned adjacent outlet 20.

The supply of pressurized gas 14 is preferably controlled to ensure that the supply remains on during normal operation. This control can also involve varying the gas flow so that the velocity of the jet exiting outlet 20 remains constant even when different sized openings are used with the housing. The range of preferred jet velocities is determined by both the density of the pressurized gas (usually air) and the mass and surface area presented by contaminants. The minimum preferred jet velocity would then be the free fall velocity of any contaminants. This can range from as little as 1 m/s for light powders or flakes to as high as 100 m/s for dense compact contaminants such as wet pulp.

Although the present invention has been described in some detail by way of example for purposes of clarity and understanding, it will be apparent that certain changes and modifications may be practised within the scope of the appended claims.

We claim:

1. Apparatus for maintaining an unobstructed view for visual monitoring equipment comprising:

a housing to isolate the visual monitoring equipment from an external environment;

an inlet to the housing connectable to a source of gas under pressure;

at least one outlet to the housing defining a view port to allow the visual monitoring equipment to acquire images external to the housing and to allow gas to exit the housing, the at least one outlet having a labyrinth passage sealing system to allow the gas through the outlet to form an exit jet that maintains the outlet open and unobstructed.

2. The apparatus of claim 1 in which the housing comprises a generally cylindrical enclosure having first and second ends, the first end being formed with the inlet and the second end being formed with the at least one outlet.

3. The apparatus of claim 1 in which the at least one outlet comprises a pinhole aperture having a diameter in the range of about 1 to 10 mm.

4. The apparatus of claim 3 in which the visual monitoring equipment comprises a camera equipped with a pinhole lens selected to match the dimensions of the pinhole aperture.

5. The apparatus of claim 1 in which the at least one outlet comprises an opening having a diameter in the range of about 11-50 mm.

6. The apparatus of claim 5 in which the visual monitoring equipment comprises a camera equipped with a 8-48 mm zoom lens selected to match the dimensions of the opening.

7. The apparatus of claim 1 in which the visual monitoring equipment is positioned adjacent the at least one aperture to achieve a wide angle view through the aperture.

8. The apparatus of claim 1 in which the visual monitoring equipment comprises a CCD array analog camera.

9. The apparatus of claim 1 in which the visual monitoring equipment comprises a CCD array digital camera.

10. The apparatus of claim 1 in which the labyrinth passage sealing system comprises:

a sealing element within the housing to separate the interior of the housing into a first region proximate the outlet into which contaminants may enter in the event that the source of gas under pressure is lost, and a second region housing the visual monitoring equipment which remains contaminant free; and a labyrinth passage about the sealing element to communicate the second region with first region to allow gas to exit the housing by the outlet, the lens of the visual monitoring equipment protruding through the sealing element into the first region.

11. The apparatus of claim 10 in which the sealing element comprises a gasket extending across the housing.

12. The apparatus of claim 11 including a gasket support member to support and retain the gasket in place.

13. The apparatus of claim 10 in which the labyrinth passage comprises an annular region about the outer perimeter of the sealing element defined by an annular shoulder having a plurality of passages dimensioned to permit the passage of gas under pressure flowing from the second region to the first region while physically blocking passage of contaminants moving from the first region to the second region.

14. The apparatus of claim 13 including a diversion element to communicate gas flowing from the second region to the first region by diverting gas flow into the annular region about the sealing element.

15. The apparatus of claim 1 in which the source of gas under pressure is a source of filtered air.

* * * * *